(12) United States Patent
Redlingshofer et al.

(10) Patent No.: US 7,402,705 B2
(45) Date of Patent: Jul. 22, 2008

(54) PRODUCTION OF 3- (ALKYLTHIO) PROPANAL

(75) Inventors: Hubert Redlingshofer, Munchsteinach (DE); Christoph Weckbecker, Grundau-Lieblos (DE); Klaus Huthmacher, Geinhausen (DE); Achim Fischer, Aschaffenburg (DE); Jan-Olaf Barth, Frankfurt am Main (DE)

(73) Assignee: Evonik Degussa GmbH, Essen (DE)

( * ) Notice: Subject to any disclaimer, the term of this patent is extended or adjusted under 35 U.S.C. 154(b) by 36 days.

(21) Appl. No.: 11/340,673

(22) Filed: Jan. 27, 2006

(65) Prior Publication Data

US 2006/0183945 A1    Aug. 17, 2006

(30) Foreign Application Priority Data

Jan. 28, 2005  (DE) ............... 10 2005 003 990

(51) Int. Cl.
 *C07C 319/00*  (2006.01)
 *C07C 321/00*  (2006.01)
 *C07C 323/00*  (2006.01)
 *C07C 381/00*  (2006.01)

(52) U.S. Cl. ............................................. 568/41
(58) Field of Classification Search ............... 568/41
   See application file for complete search history.

(56) References Cited

U.S. PATENT DOCUMENTS

| 5,387,720 | A | * | 2/1995 | Neher et al. ........... 568/486 |
| 5,705,675 | A |   | 1/1998 | Blackburn et al. |
| 5,775,329 | A |   | 7/1998 | Metzner et al. |
| 5,925,794 | A | * | 7/1999 | Hsu et al. ............... 568/41 |

FOREIGN PATENT DOCUMENTS

| DE | 42 38 493 C1 | 4/1994 |
| WO | PCT/ISA/210 | 5/2006 |

\* cited by examiner

*Primary Examiner*—Yvonne Eyler
*Assistant Examiner*—Chukwuma O Nwaonicha
(74) *Attorney, Agent, or Firm*—Pillsbury Winthrop Shaw Pittman LLP

(57) ABSTRACT

The invention relates to a process for the production of 3-(alkylthio)propanal from glycerol using catalysts.

27 Claims, No Drawings

PRODUCTION OF 3-(ALKYLTHIO) PROPANAL

Priority is claimed to Germany Patent Appl. No. 102005003990.1, file Jan. 28, 2005.

The invention relates to a process for the production of 3-(alkylthio)propanal from glycerol using catalysts.

In addition to the industrially important MMP, MMP analogues of the general form

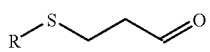

with R=H, alkyl can also be produced from glycerol.

3-(Methylthio)propanal (MMP) is an important intermediate and thus of great economic significance for the production of D,L-methionine and the methionine hydroxy analogue 2-hydroxy-4-methylthiobutyric acid (MHA). Methionine is an essential amino acid, which is used inter alia as a supplement in animal feeds. Nutrition-enhancing feed additives are now an essential component in animal nutrition. They are used to improve the utilisation of the nutrient supply, stimulate growth and promote protein formation. One of the most important of these additives is the essential amino acid methionine, which occupies a prominent position as a feed additive particularly in poultry rearing. In this field, however, so-called methionine substitutes, such as methionine hydroxy analogue (abbreviated to MHA), are also of not inconsiderable importance, since they exhibit growth-stimulating properties similar to those of the amino acid known for this purpose.

According to the prior art, MMP is produced by the catalysed addition of methyl mercaptan to acrolein. Liquid acrolein is generally reacted with methyl mercaptan in a reactor in which liquid MMP and the catalyst are already present in dissolved form (DT 2320544). The use of gaseous acrolein with methyl mercaptan is also known (FR 7520183, FR 7917827, WO 97/00858). The reaction between methyl mercaptan and acrolein can take place batchwise or continuously (U.S. Pat. Nos. 4,225,515, 5,352,837). Organic bases, e.g. tertiary amines such as hexamethylenetetramine, trialkylamines, e.g. triethyl- or triethanolamine, benzylamines, pyridines, e.g. 2-fluoropyridine and 4-dimethylaminopyridine, picoline, pyrazine, imidazole and nicotinamide, but also copper(II) acetate, mercury methyl mercaptide and organic peroxides, are used as conventional catalysts.

The use of ion exchangers has also been mentioned (FR 7520183). The actual addition catalyst is conventionally combined with an auxiliary catalyst, an organic acid, e.g. acetic acid, citric acid or formic acid, or a mineral acid, e.g. sulfuric or phosphoric acid, on the one hand to inhibit the polymerisation of acrolein, i.e. the formation of undesirable by-products, and on the other hand to increase the general yield by conditioning of the added base. The catalyst is not recovered and is lost during working up.

Typical catalyst concentrations are 0.001 to 0.005 mole %, based on methyl mercaptan. The quantity of acid, typically acetic acid, required is between 0.5 and 50 mole %. To simplify the MMP production process, the catalyst and acid can be previously combined in a premix and metered in as a solution. The concentration of catalyst premix in the liquid MMP reaction medium is generally 0.2 to 0.75 wt. %. On completion of the reaction, the MMP is separated from the auxiliary substances and by-products by distillation. During the purification by distillation of the addition product thus produced, the catalyst premix is lost and, depending on its boiling point, it has to be disposed of via the distillation bottoms or the waste gas. In principle, parts of the catalyst or the added acid can pass overhead during the distillation and contaminate the desired pure MMP.

A disadvantage of this process, besides the consumption of the catalyst, is the multi-step synthesis of MMP. Thus, the required intermediate, acrolein, has to be produced in a complex manner by selective oxidation from propene in the gas phase and isolated in a multi-step work-up.

According to the prior art, the synthesis of acrolein takes place by heterogeneously catalysed selective oxidation of propene on mixed oxide catalysts. EP 417723 describes the synthesis on complex multi-metal mixed oxide catalysts at temperatures of 300 to 380° C. and pressures of 1.4 to 2.2 bar. In Ullmann's Encyclopedia of Industrial Chemistry, 6th edition, 1999, the entire process is described, including the work-up, where several by-products are separated off. After the educt mixture of propene, air and water has been at least partly reacted on the catalyst, quenching first takes place to eliminate high-boiling by-products, such as polymers, acrylic acid and acetic acid. In the subsequent absorber, acrolein is washed out. After desorption to recover the absorbent, the crude acrolein obtained is purified by distillation in several steps.

Up to the present, glycerol has not been used for the synthesis of MMP. Furthermore, the direct synthesis of MMP from glycerol is not known. However, it is known that glycerol can be dehydrated in the presence of acidic substances to form various products.

According to Organic Synthesis I, 15-18 (1964), by treating a mixture of powdered potassium hydrogen sulfate, potassium sulfate and glycerol at 190 to 200° C., acrolein is obtained in a yield of between 33 and 48%. Because of the low yields and the high salt loads, however, this process is unsuitable for an industrial scale.

In the context of investigations into model substances of biomass pyrolysis oils, the catalytic treatment of glycerol on H-ZSM5 zeolites at 350 to 500° C. has also been investigated—cf. Dao, Le H. et al. ACS Symp. Ser.: 376 (Pyrolysis Oils Biomass) 328-341 (1988). Hydrocarbons are formed only in small yields.

In DE 42 38 493, moreover, the acid-catalysed conversion of glycerol to acrolein in the gas and in the liquid phase is described. DE 42 38 492 relates to the synthesis of 1,2- and 1,3-propanediol by dehydration of glycerol with high yields.

For the direct synthesis of MMP from glycerol, however, in addition to the involvement of dehydration steps, the simultaneous selective incorporation of a sulfur-containing compound, such as methyl mercaptan, is necessary.

According to the invention, a process particularly for the production of MMP from glycerol without the isolation of intermediates is provided, wherein the multi-step synthesis of MMP according to the prior art can now be carried out in one step using a suitable catalyst.

The invention provides a process for the production of compounds of the general formula

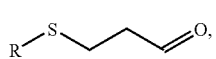

(I)

in which

R signifies H, $C_1$ to $C_3$ alkyl, by the reaction of glycerol or of a compound from which glycerol is released, with a compound of the general formula

$$R\text{---}SH \quad\quad\quad (II),$$

in which

R signifies H, $C_1$ to $C_3$ alkyl or compounds from which this (II) is produced, in the presence of a catalyst.

The preferred product is MMP, which is produced using methyl mercaptan.

In this process, for example a glycerol-methyl mercaptan mixture is reacted, optionally in the presence of a solvent, either in the liquid phase or in the gas phase, on a preferably acidic solid catalyst.

If the synthesis takes place in the liquid phase, work is carried out at a reaction temperature of between 50 and 500° C., preferably between 80 and 350° C., particularly preferably between 120 and 300° C. The pressure is adjusted such that the liquid state of the reaction mixture is maintained. The pressure is generally between 1 and 300 bar, preferably between 5 and 200 bar, particularly preferably between 20 and 150 bar. In the liquid phase, the synthesis can be carried out in the presence of either a homogeneous or preferably a heterogeneous catalyst.

In the liquid phase, the use of a solvent or diluent is also preferred. As a result of this, the concentration of glycerol is reduced and side reactions to oligomers, polymers and other high boilers are minimised. Solvents and diluents known to the person skilled in the art, such as e.g. water, alcohols, such as e.g. methanol and ethanol, acetone, toluene or methyl isobutyl ketone, are used. MMP itself can also be employed as a solvent, which has the advantage that no additional substance is used and thus the work-up is simplified.

In the reaction mixture, the glycerol concentration is between 1 and 100 wt. %, preferably between 1 and 70 wt. % and especially between 5 and 40 wt. %, based on the solvent or diluent. The molar ratio between glycerol and methyl mercaptan is adjusted to between 0.2 and 50, preferably between 0.4 and 30, especially between 0.8 and 10.

In general, a homogeneous solution is advantageous for good mass transfer, but is not absolutely essential here. This can even be exploited in a targeted manner through the principle of two-phase catalysis, in which e.g. exclusively the product MMP is soluble in the solvent phase. If the reaction product MMP is insoluble in the reaction medium, the product can be separated from the reaction medium by phase separation without a complex work-up and thus the entire process can be simplified.

If the synthesis takes place in the gas phase, the reaction is performed at a temperature of between 200 and 550° C., preferably between 220 and 450° C., particularly preferably between 250 and 350° C. The pressure is generally between 1 and 100 bar, preferably between 1 and 70 bar, particularly preferably between 1 and 30 bar. In the gas phase, the synthesis is carried out in the presence of a solid catalyst.

The use of a diluent is also preferred in the gas phase. This reduces the concentration of glycerol to the values given above, and thus side reactions forming oligomers, polymers and other high boilers are minimised. Diluents known to the person skilled in the art are used, such as e.g. nitrogen, air or water. Diluting media that can be simply isolated from MMP by phase separation after condensation are preferred.

Regardless of whether the process takes place in the gas or liquid phase, by using glycerol as a raw material the concentration of reactive intermediates, such as possibly acrolein, allyl alcohol, acrolein acetals, 3-hydroxy-propanal or radical and ionic compounds with three carbon atoms, is adjusted to a comparatively low level by further reaction to MMP, since these intermediates can undergo rapid further reaction to form MMP. A high concentration of reactive intermediates would lead to increased formation of high-boiling residues and is therefore undesirable. However, according to the prior art, for example, acrolein is still worked up in a high concentration and used as an isolated intermediate.

Moreover, through the conversion of glycerol to dehydrated reactive compounds, which undergo rapid further reaction in the presence of methyl mercaptan to form MMP, very high conversions of glycerol are possible without the formation of high-boiling by-products.

MMP that has formed can then be separated out of the reaction mixture by a known method, alone or together with part of the solvent or diluent medium, by stripping, distillation or extraction. Unreacted glycerol can then be recycled into the reaction step.

Another advantage of the process lies in the fact that even glycerol solutions with a content of 5 to 40 wt. % can be used. Thus, so-called crude glycerols may be employed directly for the synthesis of MMP without previous concentration or purification.

The implementation can be carried out in reaction vessels known to the person skilled in the art, such as e.g. fixed bed reactors, stirred vessels, stream tubes or bubble columns.

Methyl mercaptan can be used here in either liquid or gaseous form. Moreover, it can be employed as a pure substance or as crude methyl mercaptan with impurities, such as e.g. methanol, dimethyl sulfide, dimethyl polysulfides, hydrogen sulfide or dimethyl ether. The use of crude methyl mercaptan has the advantage that a cheaper raw material can be employed, requiring no further working up.

Insoluble substances which, in addition to the dehydration of glycerol, at the same time selectively accelerate the incorporation of methyl mercaptan into MMP are generally used as acidic heterogeneous catalysts. These preferably have an $H_0$ value of less than +2, especially less than −3. The $H_0$ value corresponds to the Hammett acidity function and can be determined by so-called amine titration using indicators or by adsorption of a gaseous base—cf. Studies in surface science and catalysis, vol. 51, 1989: "New solid acids and bases, their catalytic properties", K. Tanabe et al., chapter 2, especially pages 5-9, chapter 1 (pages 1-3) of the above document mentions numerous solid acids from which the person skilled in the art, optionally after determining the $H_0$ value, can select a suitable catalyst. Suitable catalysts are preferably (i) natural or synthetic siliceous substances, such as in particular mordenite, montmorillonite and acidic zeolites, such as e.g. HZSM-5, MCM-22, zeolite beta; (ii) support materials, such as oxidic or silicalitic substances, e.g. aluminium oxide, titanium oxide, silicon oxide, zirconium oxide or mixtures thereof coated with mono-, di- or polybasic inorganic acids, especially phosphoric acid, sulfuric acid or acid salts of inorganic acids; (iii) oxides and mixed oxides, such as e.g. aluminium oxides, zinc oxide-aluminium oxide mixtures or heteropolyacids.

The process can be carried out in the liquid or in the gas phase. In principle, the same acid catalysts can be used in both embodiments. However, it has been demonstrated that some catalysts are preferably suitable for the gas phase and others are preferably suitable for the liquid phase.

Thus, in the liquid phase, it is preferable to use acidic zeolites because of their $H_0$ value of less than −3. In the gas phase, on the other hand, they are subject to more rapid deactivation, which reduces the space-time yield.

Oxides and mixed oxides, on the other hand, provide the better yields in the gas phase.

When carrying out the conversion of glycerol to MMP in the liquid phase, correspondingly acidic homogeneous catalysts, which are soluble in the reaction mixture, can also be used. These homogeneous catalysts can be used alone or in combination with one of the heterogeneous catalysts described here.

In another embodiment of the invention, methyl mercaptan is not added to the reaction mixture immediately at the beginning of the reaction but is fed in only after reactive intermediates have formed under the conditions stated above, at least from partial quantities of glycerol. The reactive intermediates form MMP by further reaction after methyl mercaptan has been added. On the one hand, this method facilitates the conversion of glycerol to dehydrated reactive intermediates and reduces non-selective reactions between glycerol and methyl mercaptan. As a result, the MMP yield can be improved. At the same time, moreover, by carrying out the reaction in this way, the complex separation of acrolein according to the prior art can be avoided and the reaction to MMP conducted in one reactor.

This can take place on the one hand in a batchwise process, the methyl mercaptan being added to the reaction mixture after a certain reaction period. A stirred vessel, for example, would be suitable for this implementation. A further possibility is a semi-continuous method, in which the glycerol solution and the catalyst are the initial charge and the methyl mercaptan is metered in continuously.

On the other hand, it is also possible to feed in methyl mercaptan only at a point removed from the reactor entrance in the direction of flow or in another section of the reactor. By the time the glycerol solution and the catalyst reach this point, part of the glycerol has already been converted to reactive intermediates. This method can be implemented industrially e.g. in a staged reactor with intermediate feed, a stirred vessel cascade or a stream tube.

Another advantage of the delayed or later addition of at least a major portion of the methyl mercaptan lies in the fact that the yield of MMP can be increased, because the temperature profile or temperature program can be adjusted so that it is optimised on the basis of the reaction behaviour of the reactants. Thus, the activation of glycerol and its first dehydration step require a very high activation energy and thus high reaction temperatures for rapid production with high space-time yields. MMP, on the other hand, has a tendency towards non-selective further reactions at temperatures higher than approx. 100 to 150° C. Thus, conducting the conversion of glycerol to MMP by passing through decreasing reaction temperatures represents a preferred embodiment.

EXAMPLES

Example 1

In an autoclave, 36 g glycerol and 19.5 g methyl mercaptan were dissolved in 144 g methanol. 3.8 g of zeolite HZSM-5, modulus 28 ($H_0$<−8.2), were added to this mixture. The zeolite was calcined for 2 h at 150° C. and 4 h at 500° C. in air in a drying oven before charging into the autoclave. The mixture was then heated to 300° C. in the autoclave, with stirring. During this operation, a pressure of 61 bar was established. After one hour, a sample was taken from the mixture and analysed by gas chromatography. Taking into account the proportion of solvent, the MMP content was 6.0 wt. %. None of the by-products or intermediates acrolein and allyl alcohol could be detected.

Example 2

In an autoclave, 36 g of glycerol were dissolved in 80 g of methanol. 3.8 g of zeolite ammonium beta CP 814E ($H_0$<−3.0) from Zeolyst International were added to this mixture. The zeolite was calcined for 2 h at 150° C. and 4 h at 500° C. in air in a drying oven before charging into the autoclave. The mixture was then heated within 4 h and stirred at 300° C. and 40 bar. After cooling to room temperature, 19.5 g of methyl mercaptan and 68 g of methanol were added. This new mixture was then heated to 100° C. in an autoclave, with stirring. During this operation, a pressure of 3 bar was established. After 30 min, a sample was taken from the mixture and analysed by gas chromatography. Taking into account the proportion of solvent, the MMP content was 0.8 wt. %.

The invention claimed is:

1. A process of producing a compound of formula (I):

(I)

wherein R represents H or a $C_1$-$C_3$ alkyl,
comprising reacting:
(a) glycerol with
(b) a compound of formula (II):

(II)

wherein $R^1$ represents H or a $C_1$-$C_3$ alkyl;
wherein said reaction of glycerol with (b) above is conducted in the presence of a catalyst.

2. The process of claim 1, wherein the compound of formula (I) is 3-(methylthio)propanal and wherein $R^1$ of formula (II) is methyl.

3. The process of claim 1, wherein the catalyst is an acidic solid catalyst having an $H_0$ value of less than +2.

4. The process of claim 1, wherein the molar ratio of component (a) to component (b) ranges from 0.2:1 to 50:1.

5. The process of claim 1, further comprising the use of a solvent or diluent.

6. The process of claim 5, wherein the amount of component (a) used ranges from 1 to 100 wt. %, based on the amount of solvent or diluent.

7. The process of claim 6, wherein the amount of component (a) used ranges from about 1 to about 70 wt. %, based on the amount of solvent or diluent.

8. The process of claim 5, wherein the solvent or diluent is 3-(methylthio)propanal.

9. The process of claim 5, wherein the solvent or diluent is water.

10. The process of claim 5, wherein the solvent or diluent is methanol.

11. The process of claim 1, wherein the process takes place in the liquid phase.

12. The process of claim 11, wherein the process takes place at pressures ranging from about 1 to about 300 bar and at temperatures ranging from 20 to 500° C.

13. The process of claim 11, wherein the catalyst is an acidic zeolite.

14. The process of claim 11, wherein the catalyst is a homogenous catalyst.

15. The process of claim 14, wherein the process takes place at pressures ranging from 1 to 300 bar and at temperatures ranging from −10 to 500° C.

16. The process of claim 1, wherein the process takes place in the gas phase.

17. The process of claim 16, wherein the process takes place at pressures ranges from 1 to 100 bar and at temperatures ranging from 200 to 550° C.

18. The process of claim 16, wherein the catalyst has an $H_0$ value of less than −3.

19. A process of producing a compound of formula (I):

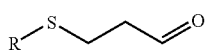

(I)

wherein R represents methyl,
comprising reacting:
(a) glycerol, with
(b) methyl mercaptan,
in the presence of a catalyst.

20. The process of claim 19, wherein the glycerol has been first added to the catalyst in a reaction mixture for a time sufficient so that at least part of the glycerol has been converted to an intermediate.

21. The process of claim 20, wherein the methyl mercaptan is added to the reaction mixture in a batchwise process or the methyl mercaptan is metered into the reaction mixture in a semi-continuous process.

22. The process of claim 21, wherein the reaction takes places in at least two spatially separate reaction zones, the glycerol being at least partially converted in a first reaction zone, and the methyl mercaptan being introduced into the reaction mixture in a second reaction zone.

23. The process of claim 22, wherein the first reaction zone is conducted at a temperature range of from about 150 to about 400° C., and the second reaction zone is conducted at a temperature range of from about 0 to about 100° C.

24. The process of claim 22, wherein the first reaction zone is cooled to about 20° C. to about 150° C. before the majority of the methyl mercaptan is introduced into the reaction mixture.

25. The process according to claim 1, wherein said glycerol is released from a precursor of glycerol.

26. The process according to claims 25, wherein said precursor of glycerol is a mono-, di- or triglyceride.

27. The process according to claim 26, wherein said mono-, di- or triglyceride is a $C_2 C_{20}$ aliphatic carboxylic acid ester of glycerol.

* * * * *